United States Patent [19]

Bach et al.

[11] 4,031,097

[45] June 21, 1977

[54] DESCARBOXYLYSERGIC ACID

[75] Inventors: Nicholas J. Bach; David A. Hall; Edmund C. Kornfeld, all of Indianapolis, Ind.

[73] Assignee: Eli Lilly and Company, Indianapolis, Ind.

[22] Filed: Nov. 3, 1975

[21] Appl. No.: 628,306

Related U.S. Application Data

[60] Division of Ser. No. 504,395, Sept. 9, 1974, Pat. No. 3,954,772, which is a continuation-in-part of Ser. No. 389,281, Aug. 17, 1973, abandoned.

[52] U.S. Cl. .............................. 260/285.5; 424/261
[51] Int. Cl.² ...................................... C07D 457/00
[58] Field of Search ................................ 260/285.5

[56] References Cited

UNITED STATES PATENTS 3,954,772  5/1976  Bach et al. ...................... 260/285.5

OTHER PUBLICATIONS

Kline; J. Org. Chem., vol. 25, pp. 142–143, (1960).
Abe et al.; Bull. Chem. Soc., Japan, vol. 20, pp. 95–96, (1956).

*Primary Examiner*—Donald G. Daus
*Assistant Examiner*—Mary C. Vaughn
*Attorney, Agent, or Firm*—James L. Rowe; Everet F. Smith

[57] ABSTRACT

Descarboxylysergic acid prepared from 2,3-dihydro-8β-hydroxy-6-methyl-9-ergolene or from penniclavine has oxytocic, serotonin antagonist, prolactin inhibition and muscle contracting activities.

3 Claims, No Drawings

DESCARBOXYLYSERGIC ACID

CROSS-REFERENCE

This application is a division of our copending application Ser. No. 504,395 filed Sept. 9, 1974, now U.S. Pat. No. 3,954,772, issued May 4, 1976, which was, in turn, a continuation-in-part of our then copending application Ser. No. 389,281, filed Aug. 17, 1973, now abandoned.

BACKGROUND OF THE INVENTION

Compounds based on the ergoline ring system:

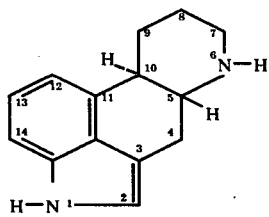

have a surprising variety of pharmaceutical activities. For example, lysergic and isolysergic acid are 8-carboxy-6-methyl-9-ergolenes. The amides of lysergic acid, many of which have valuable and unique pharmacologic properties, include the naturally occurring oxytocic alkaloids — ergocornine, ergokryptine, ergonovine, ergocristine, ergosine, ergotamine, etc. — and synthetic oxytocics such as methergine as well as the synthetic hallucinogen — lysergic acid diethylamine or LSD. The amides of 6-methyl-8-carboxyergoline, known generically as dihydroergot alkaloids, are oxytocic agents of lower potency and also lower toxicity than the ergot alkaloids themselves. Recently, it has been found by Clemens, Semonsky, Meites, and their various co-workers that many ergot-related drugs have activity as prolactin inhibitors including ergocornine, dihydroergocornine, 2-bromo-α-ergokryptine and d-6-methyl-8-cyanomethylergoline. References embodying some of the newer findings in the field of ergoline chemistry are the following: Nagasawa and Meites, Proc. Soc. Exp't'l. Biol. Med. 135, 469 (1970); Lutterbeck et al., Brit. Med. J., 228, (July 24, 1971); Heuson et al., Europ. J. Cancer, 353 (1970); Coll. Czech, Chem. Commun., 33, 577 (1968); Nature, 221, 666 (1969); Seda et al., J. Reprod. Fert., 24, 263 (1971); Mantle and Finn, id, 441; Semonsky and co-workers, Coll. Czech. Chem. Comm., 36, 2200 (1971); Schaar and Clemens, Endocr., 90, 285–8 (1972); Clemens and Schaar, Proc. Soc. Exp. Biol Med., 139, 659–662 (1972) and Sweeney, Clemens, Kornfeld and Poore, 64th Annual Meeting, American Association Cancer Research, April 1973. Recently issued patents in the field of ergoline derivatives or lysergic acid derivatives include the following: U.S. Pat. No. 3,704,233, U.S. Pat. No. 3,709,891, U.S. Pat. No. 3,585,201, U.S. Pat. No. 3,666,762, U.S. Pat. No. 3,586,683, U.S. Pat. No. 3,717,640, and U.S. Pat. No. 3,592,816.

A number of the non-peptide indole alkaloids have been found in fungus cultures grown on *Elymus nollis* and other related grasses. These non-peptide alkaloids include chanoclavine, agroclavine, elymoclavine, and penniclavine. Of particular interest are agroclavine, an 8-methyl-8-ergolene; elymoclavine, an 8-hydroxymethyl-8-ergolene, and penniclavine, an 8-hydroxymethyl-8-hydroxy-9-ergolene. These non-peptide alkaloids have been shown to have potent rat prolactin inhibiting activity comparable to that found with the peptide alkaloid, ergocornine.

D-6,8-dimethyl-9-ergolene has been prepared as one of seven related products by the reduction of elymoclavine with sodium in n-butanol according to Yamatodani and Abe, *Bull. Agr. Soc. Japan*, 20, 95 (1956). Descarboxylysergic acid has not hitherto been described, and there is no method known in the art for removing the 8-methyl group from D-6,8-dimethyl-9-ergolene to produce descarboxylysergic acid.

SUMMARY OF THE INVENTION

This invention provides DL-descarboxylysergic acid and the optically active D isomer, all represented by the formula:

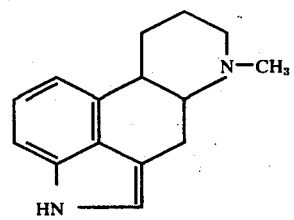

I

The racemate, DL-descarboxylysergic acid, is prepared by two alternate routes starting with 2,3-dihydro-8β-hydroxy-6-methyl-9-ergolene [prepared by the method of Kornfeld et al., (*J. Am. Chem. Soc.*, 78, 3087 (1956))].

In the first of these routes, the 2,3-dihydro-8β-hydroxy-6-methyl-9-ergolene (Formula II wherein R is H and R' is OH)

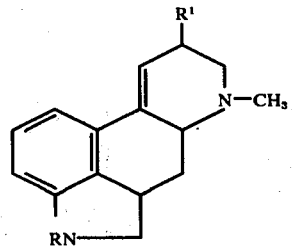

II is oxidized at the 8-hydroxyl group with manganese dioxide in an inert solvent to give the corresponding 6-methyl-9-ergolene-8-one (III).

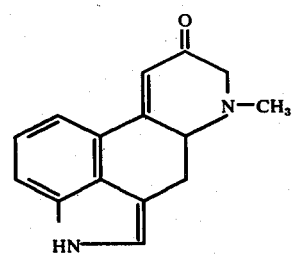

III

Conversion of the ketone to the corresponding ethylene dithioketal is accomplished by reaction with ethanedithiol in the presence of borontrifluoride etherate or other Lewis acid. The dithioketal is then readily desulfurized by the action of Raney nickel according to the procedure of Stutz and Stadler (*Helv. Chim. Acta*, 55, 75 (1972)) to yield DL-descarboxylysergic acid (Formula I).

The alternate procedure involves the reaction of 2,3-dihydro-8β-hydroxy-6-methyl-9-ergolene (II wherein R is H and R' is OH) with acetic anhydride to yield the corresponding 1-acetyl-2,3-dihydro-6-methyl-8β-acetoxy-9-ergolene (II wherein R' is O-Ac and R is Ac). Electrochemical reduction of this compound at −2.30 volts versus methanolic S.C.E. at a mercury pool cathode gives the corresponding 1-acetyl-9,10-didehydro-2,3-dihydro-6-methylergoline (II wherein R is Ac and R' is H). Hydrolysis of the amide to remove the 1-acetyl group followed by manganese dioxide oxidation as above yields the desired DL-descarboxylysergic acid(I).

The optically-active D-isomer, D-descarboxylysergic acid, represented by I above is prepared from the naturally-occurring ergot alkaloid, penniclavine represented by Structure IV below, also by either of two alternate procedures.

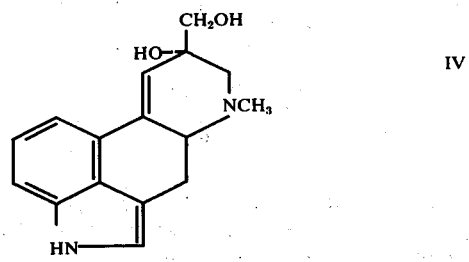

IV

Oxidation of penniclavine with periodate yields the D-ketone, D-9,10-didehydro-6-methylergoline-8-one (D-6-methyl-9-ergolene-8-one) represented by Structure III above. The ketone represented by III is converted to the dithioketal which is desulfurized to give D-descarboxylysergic acid. An alternate procedure involves the reduction of the ketone (III) to yield D-6-methyl-8-hydroxy-9-ergolene. Acetylation with acetic anhydride or the like reagent yields the 8-acetoxy derivative which is then readily reduced electrochemically under the conditions specified above for the electrochemical reduction of 1-acetyl-2,3-dihydro-6-methyl-9-ergolene. D-descarboxylysergic acid is the product of either preparative route.

Penniclavine itself is a naturally occurring alkaloid and is found in small quantities in ergoted grain. Recently, however, procedures have been developed for the synthesis of penniclavine from D-lysergic acid which can be produced in abundant quantities by the submerged culture fermentation of *Claviceps paspali* and other related organisms. According to these procedures as set forth in the copending application of Kornfeld and Bach, Ser. No. 494,147 filed Aug. 2, 1974, now U.S. Pat. No. 3,929,796, and of Bernardi and by Temperilli, International Union of Pure and Applied Chemistry, 9th Symposium on the Chemistry of Natural Products, Ottawa, Province of Ontario, Canada, June 24–28, 1974, D-6-methyl-8-carbomethoxy-10α-methoxy-8-ergolene as furnished by the procedure of U.S. Pat. No. 3,814,765 is reduced with a metal hydride reducing agent to the corresponding D-6-methyl-8-hydroxymethyl-10α-methoxy-8-ergolene which can be rearranged under acidic conditions to yield penniclavine.

As previously stated, DL-descarboxylysergic acid and the D-isomer are pharmacologically active, having an ability to contract the isolated rabbit aorta about equal to that of ergonovine, a naturally occurring ergot alkaloid. The DL-compound is also about 1/10th as active as ergonovine in contracting the rabbit uterus, a standard test for oxytocic action. The $ED_{50}$ of DL-descarboxylysergic acid as a serotonin antagonist using an isolated rat stomach strip was 0.03 µg/ml (about ⅓ the potency of methysergide). In the prolactin inhibition assay, DL-descarboxylysergic acid is active, though less than 10 percent as active as ergocornine, another naturally occurring ergot alkaloid and one of the more powerful of the prolactin inhibiting alkaloids. In addition, the DL-racemate demonstrates a hypotensive action in anesthetized cats and in non-anesthetized dogs at very low dose levels. Finally, the mouse behavior screen indicates that DL-descarboxylysergic acid, at higher doses than those seen with the above pharmacologic activities, has an effect on the central nervous system similar to that seen with lysergic acid diethyl amide, indicating a potential ability to cause hallucinations. The optically-active isomer, D-descarboxylysergic acid is generally about twice as active as the DL-racemate in the above standard pharmacologic tests.

This invention is more specifically illustrated by the following examples.

EXAMPLE 1

Preparation of DL-descarboxylysergic acid

A solution containing 2 g. of 2,3-dihydro-8β-hydroxy-6-methyl-9-ergolene in 500 ml. of chloroform was prepared. About 28 g. of manganese dioxide were added, and the reaction mixture was stirred for about two hours. The manganese dioxide was separated by filtration, and the filter cake was washed several times with hot chloroform. The combined filtrates were concentrated and the concentrate chromatographed over 30 g. of florisil. 6-Methyl-9-ergolene-8-one produced in the above reaction was eluted with chloroform containing 5 percent ethanol. Crystallization of the product from an ether-hexane solvent mixture yielded DL-6-methyl-9-ergolene-8-one melting at about 145°–148° C. with decomposition.

Analysis: $C_{15}H_{14}N_2O$ (238.3). Calcd.: C, 75.61; H, 5.92; N, 11.76. Found: C, 75.50; H, 6.15; N, 11.85.

A suspension of 0.33 g. of DL-6-methyl-9-ergolene-8-one, 1.0 ml. of ethane dithiol and 0.5 ml. of borontrifluoride etherate was stirred for 19 hours under a nitrogen atmosphere. Chloroform, methanol and water were added to dissolve the constituents of the mixture, and the resulting two-layer system made basic by the addition of aqueous saturated sodium bicarbonate. The chloroform layer was separated and dried, and the chloroform removed therefrom by evaporation in vacuo. The resulting residue, comprising DL-6-methyl-9-ergolene-8-one ethylenedithioketal, was dissolved in chloroform, and the solution filtered through fluorosil. Removal of the chloroform solvent yielded a residue which melted at 190°–193° C. with decomposition after recrystallization from hexane.

Analysis: $C_{17}H_{18}N_2S_2$ (314.5). Calcd.: C, 64.93; H, 5.77; N, 8.91; S, 20.39. Found: C, 64.67; H, 5.83; N, 8.66; S, 20.50.

A suspension of 7 ml. of Raney nickel prepared by the method of Stutz and Stadler (Loc. cit) in 16 ml. of acetone and 4 ml. of dimethylformamide (DMF) was prepared. The suspension was added to a solution of 0.35 g. of the above dithioketal dissolved in 15 ml. of DMF. The reaction mixture was stirred for one hour.

The nickel was separated by filtration. The filtrate was diluted with water. DL-descarboxylysergic formed in the above reaction was extracted into ethyl acetate, and the ethyl acetate layer separated, washed with water and dried. Removal of the ethyl acetate by evaporation in vacuo yielded a residue which was dissolved in chloroform and filtered over 25 g. of florisil. DL-descarboxylysergic acid was eluted with chloroform containing 5 percent ethanol. The compound melted above 200° C. with decomposition after recrystallization from ethanol.

Analysis: $C_{15}H_{16}N_2$ (224.3). Calcd.: C, 80.32; H, 7.19; N, 12.49. Found: C, 80.49; H, 7.02; N, 12.47.

DL-descarboxylysergic acid maleate was prepared in tetrahydrofuran solution. Recrystallization of the salt from ethanol yielded DL-descarboxylysergic acid maleate melting at about 183°–5° C. with decomposition.

Analysis: $C_{19}H_{20}N_2O_4$ (340.4). Calcd.: C, 67.05; H, 5.92; N, 8.23. Found: C, 67.27; H, 6.17; N, 8.52.

EXAMPLE 2

Alternate preparation of DL-descarboxylysergic acid

Ten grams of DL-2,3-dihydro-8β-hydroxy-6-methyl-9-ergolene were dissolved in 325 ml. of warm acetic anhydride, and the resulting solution was stirred for about 16 hours. The reaction mixture was poured into water, and the aqueous layer made basic with saturated aqueous sodium bicarbonate. DL-1-acetyl-2,3-dihydro-6-methyl-8β-acetoxy-9-ergolene produced in the above reaction was extracted into chloroform, and the extract separated and washed with water. The extract was dried, and the chloroform removed therefrom by evaporation in vacuo. The resulting residue, comprising DL-1-acetyl-2,3-dihydro-6-methyl-8β-acetoxy-9-ergolene, melted at about 174°–177° C. after recrystallization from chloroform-ether solvent mixture.

Analysis: $C_{19}H_{22}N_2O_3$ (326.3). Calcd.: C, 69.92; H, 6.79; N, 8.58. Found: C, 69.71; H, 6.86; N, 8.36.

A solution of 2 g. of DL-1-acetyl-2,3-dihydro-6-methyl-8β-acetoxy-9-ergolene prepared as above was dissolved in 100 ml. of an electrolyte consisting of a 0.1 M tetraethylammonium chloride solution in a 9 percent by volume water: reagent grade DMF solvent. The solution was electrolyzed at −2,3 volts versus the methanolic S.C.E. at a mercury pool cathode separated by a fine glass frit from a Pt anode; the number of coulombs which passed corresponded to a 2 electron transfer. The reduction product was isolated by evaporation of the electrolyte in vacuo, slurrying the residue in saturated aqueous sodium bicarbonate, and extracting the product, DL-1-acetyl-2,3-dihydro-6-methyl-9-ergolene, with ethyl acetate. The ethyl acetate extract was separated, washed with water and dried. Evaporation of the solvent yielded DL-1-acetyl-2,3-dihydro-6-methyl-9-ergolene. The crude compound was converted to the maleate salt which melted at about 181°–182° C. with decomposition after recrystallization from ethanol-ether.

Analysis: $C_{21}H_{24}N_2O_5$ (384.4). Calcd.: C, 65.61; H, 6.29; N, 7.29. Found: C, 65.36; H, 6.05; N, 7.48.

A solution containing 1.3 g. of DL-1-acetyl-2,3-dihydro-6-methyl-9-ergolene, 5 g. of potassium hydroxide, and 5 ml. of 85 percent hydrazine in 115 ml. of ethylene glycol was heated at refluxing temperature for about 15 hours. The reaction mixture was then cooled, diluted with water, and DL-2,3-dihydro-6-methyl-9-ergolene, formed in the above hydrolysis procedure, extracted with chloroform. The chloroform extract was separated and dried. Evaporation of the chloroform yielded DL-2,3-dihydro-6-methyl-9-ergolene melting at about 171°–172° C. after recrystallization from an ethanol-hexane solvent mixture.

Analysis: $C_{15}H_{18}N_2$ (226.3). Calcd.: C, 79.61; H, 8.02; N, 12.38. Found: C, 79.80; H, 7.99; N, 12.64.

A mixture containing 1.5 g. of DL-2,3-dihydro-6-methyl-9-ergolene and 10 g. of manganese dioxide in 500 ml. of chloroform was stirred for about 2.5 hours under a nitrogen atmosphere. The resulting solid was separated by filtration and the filter cake washed several times with a hot chloroform:ethanol (3:1) solvent mixture. The filtrates were combined and the solvent evaporated therefrom in vacuo. The resulting residue was dissolved in chloroform and chromatographed over 30 g. of florisil. DL-descarboxylysergic acid formed in the above reaction was eluted with chloroform containing 1 percent ethanol. Recrystallization of the product from ether yielded purified DL-descarboxylysergic acid.

EXAMPLE 3

Preparation of D-6-Methyl-8-ergolene-8-one

A solution containing 345 mg. of periodic acid was prepared in 25 ml. of water. 450 mg. of penniclavine were added. The reaction mixture was stirred at room temperature under a nitrogen atmosphere for about 1 hour and was then poured into saturated aqueous sodium bicarbonate. D-6-methyl-9-ergolene-8-one formed in the above reaction was insoluble in the alkaline layer and was extracted with ethyl acetate. The ethyl acetate layer was separated, washed with saturated aqueous sodium chloride and dried. Evaporation of the organic solvent yielded a residue comprising D-6-methyl-9-ergolene-8-one which was purified by chromatography over 30 g. of florisil using chloroform containing 1 percent methanol as an eluant. Chromatographic fractions containing D-6-methyl-9-ergolene-8-one as shown by thin layer chromatography were combined and the solvent evaporated in vacuo. Recrystallization of the resulting residue yielded D-6-methyl-9-ergolene-8-one, melting at 149°–151° C. with decomposition.

EXAMPLE 4

Preparation of D-6-methyl-8-hydroxy-9-ergolene

A solution was prepared containing 320 mg. of D-6-methyl-9-ergolene-8-one in 75 ml. of methanol and 5 ml. of water. About 500 mg. of sodium borohydride were added and the subsequent mixture stirred at room temperature for 20 minutes. Color disappeared from the reaction after 10 minutes. The reaction mixture was poured into a mixture of ammonium hydroxide and water, and the alkali-insoluble material extracted with chloroform. Chloroform extraction was continued until a negative Van Urk test was obtained. The chloroform extracts were combined. The combined extracts were washed with saturated aqueous sodium chloride, dried and the chloroform evaporated therefrom. The residue comprising D-6-methyl-8-hydroxy-9-ergolene formed in the above reaction was recrystallized from a chloroform-methanol solvent mixture and melted at about 225° C. with decomposition.

Analysis Calcd.: C, 74.97; H, 6.71; N, 11.66; Found: C, 75.24; H, 6.67; N, 11.46.

EXAMPLE 5

Preparation of D-6-methyl-8-acetoxy-9-ergolene

Example 2 was repeated except that 900 mg. of D-6-methyl-9-ergolene-8-one were employed. 755 mg. of D-6-methyl-8-hydroxy-9-ergolene were obtained after evaporation of the chloroform from the combined chloroform extracts and this residue was acetylated by dissolution in 75 ml. of pyridine and 75 ml. of acetic anhydride. The acetylation mixture was stirred at room temperature for 3.5 hours and then poured over ice. The aqueous layer was made strongly basic with 10 percent aqueous ammonium hydroxide and the subsequent alkaline layer extracted with ethyl acetate. The ethyl acetate layer was separated and washed several times with water followed by a wash with saturated aqueous sodium chloride. The layer was dried and ethyl acetate evaporated therefrom to yield as a residue D-6-methyl-8-acetoxy-9-ergolene which melted at 151°–5° C. with decomposition after recrystallization from methanol.

Analysis Calcd.: C, 72.30; H, 6.42; N, 9.92; Found: C, 72.39; H, 6.15; N, 9.78.

In the above reaction, other alkanoyloxy derivatives at C-8 can be prepared by using appropriate acylating agents. In particular, the 8-propionyloxy, 8-butyryloxy and 8-isobutyryloxy derivatives, [the lower alkanoyloxy,

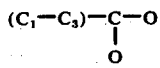

can be prepared by using propionic anhydride or isobutyric anhydride in place of acetic anhydride in the above example.

EXAMPLE 6

Preparation of D-descarboxylysergic acid

A solution was prepared containing 200 mg. of D-6-methyl-8-acetoxy-9-ergolene in 10 ml. of a 9:1 DMF-water solvent mixture saturated with sodium bicarbonate. The solution was electrolyzed at −2.325 volts vs. the methanolic S.C.E. at a mercury pool cathode separated by a fine glass frit from a platinum anode; the number of coulombs which were passed corresponded to a 2-electron transfer. After the electrolysis had been completed, the reduction product was isolated by dilution with water followed by extraction with ethyl acetate of the D-descarboxylysergic acid formed in the above reduction. The ethyl acetate layer was separated, washed with water and with saturated aqueous sodium chloride and then dried. Evaporation of the solvent left D-descarboxylysergic acid as a residue. The residue was dissolved in THF and an excess of maleic acid in ether added. D-descarboxylysergic acid maleate thus formed crystallized and melted at 192°–3° C. with decomposition after recrystallization from ether.

Analysis Calcd.: C, 67.05; H, 5.92; N, 8.23; Found: C, 66.80; H, 5.80; N, 7.98.

We claim:
1. Descarboxylysergic acid.
2. A racemate according to claim 1, said racemate being DL-descarboxylysergic acid.
3. An optical isomer of a compound according to claim 1, said isomer being d-descarboxylysergic acid.

* * * * *